United States Patent [19]
Amidon et al.

[11] Patent Number: 5,387,421
[45] Date of Patent: Feb. 7, 1995

[54] MULTI STAGE DRUG DELIVERY SYSTEM

[75] Inventors: Gordon L. Amidon; Glen D. Leesman; Lizbeth B. Sherman, all of Ann Arbor, Mich.

[73] Assignee: TSRL, Inc., Ann Arbor, Mich.

[21] Appl. No.: 251,731

[22] Filed: May 31, 1994

Related U.S. Application Data

[63] Continuation of Ser. No. 826,253, Jan. 27, 1992, abandoned, which is a continuation of Ser. No. 648,968, Jan. 31, 1991, abandoned.

[51] Int. Cl.$^6$ .............................................. A61K 9/22
[52] U.S. Cl. ..................... 424/472; 424/453; 424/464; 424/466; 424/468; 424/470
[58] Field of Search ............... 424/464, 451, 453, 466, 424/468, 470, 472

[56] References Cited

U.S. PATENT DOCUMENTS 4,865,849  9/1989  Conte ................................. 424/470

FOREIGN PATENT DOCUMENTS 2230441  10/1990  United Kingdom .

Primary Examiner—G. S. Kishore
Assistant Examiner—Raj Bawa
Attorney, Agent, or Firm—Reising, Ethington, Barnard, Perry & Milton

[57] ABSTRACT

A drug delivery system includes a first capsule half having an inner chamber for containing a drug therein. A plug is disposed in a passageway of the capsule half for plugging the opening thereof. The plug is releasable from the passageway opening upon the application of pressure from within the inner chamber. A pump mechanism causes an increase in pressure within the inner chamber and forces the plug out of the passageway to release the drug from the inner chamber and out of the passageway thereby providing a second pulse of drug release at a predetermined time after initial ingestion of the capsule. The invention further provides a method of manufacturing the drug delivery system and method by which the drug delivery system provides the drug to the body.

18 Claims, 6 Drawing Sheets

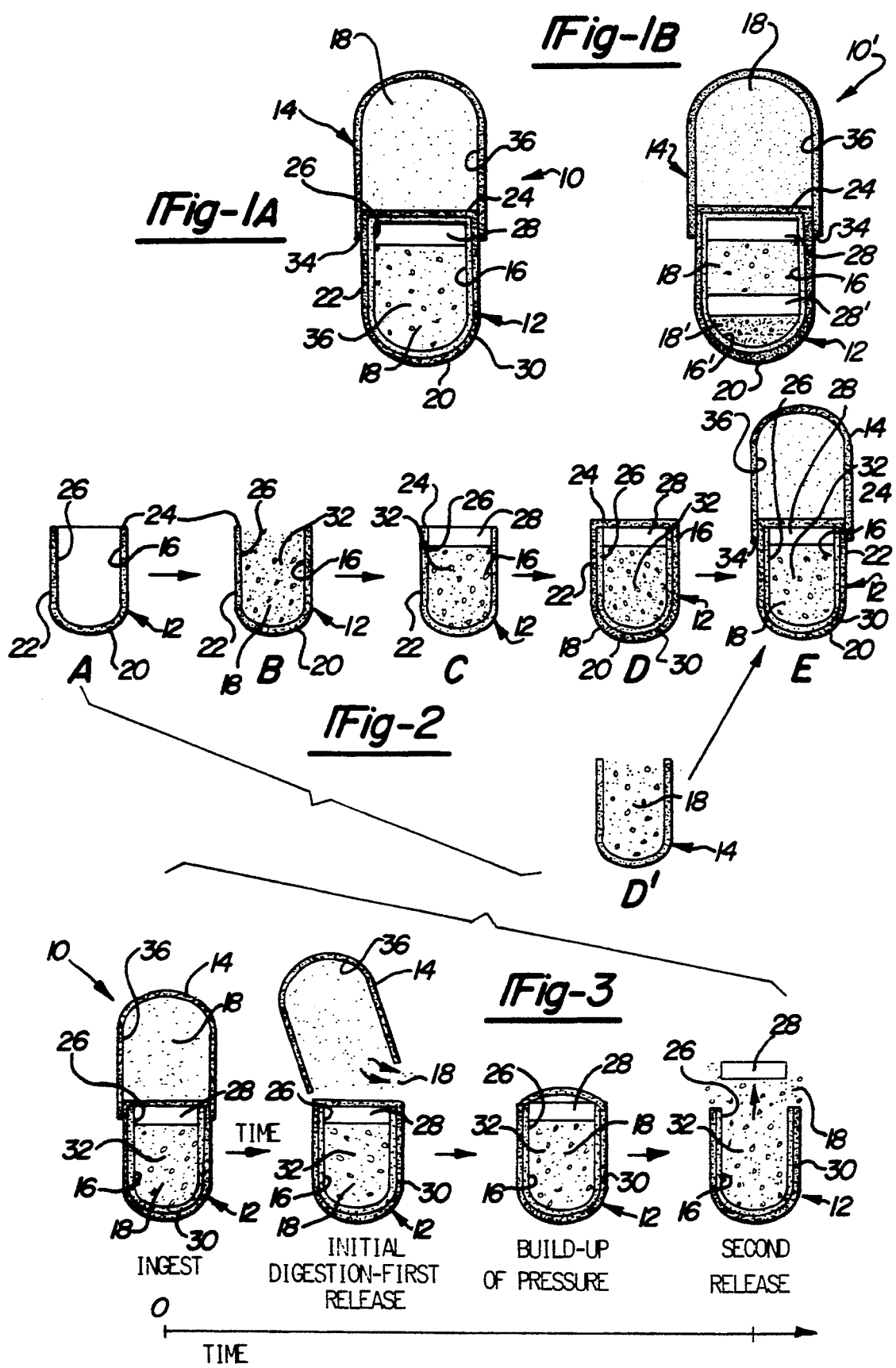

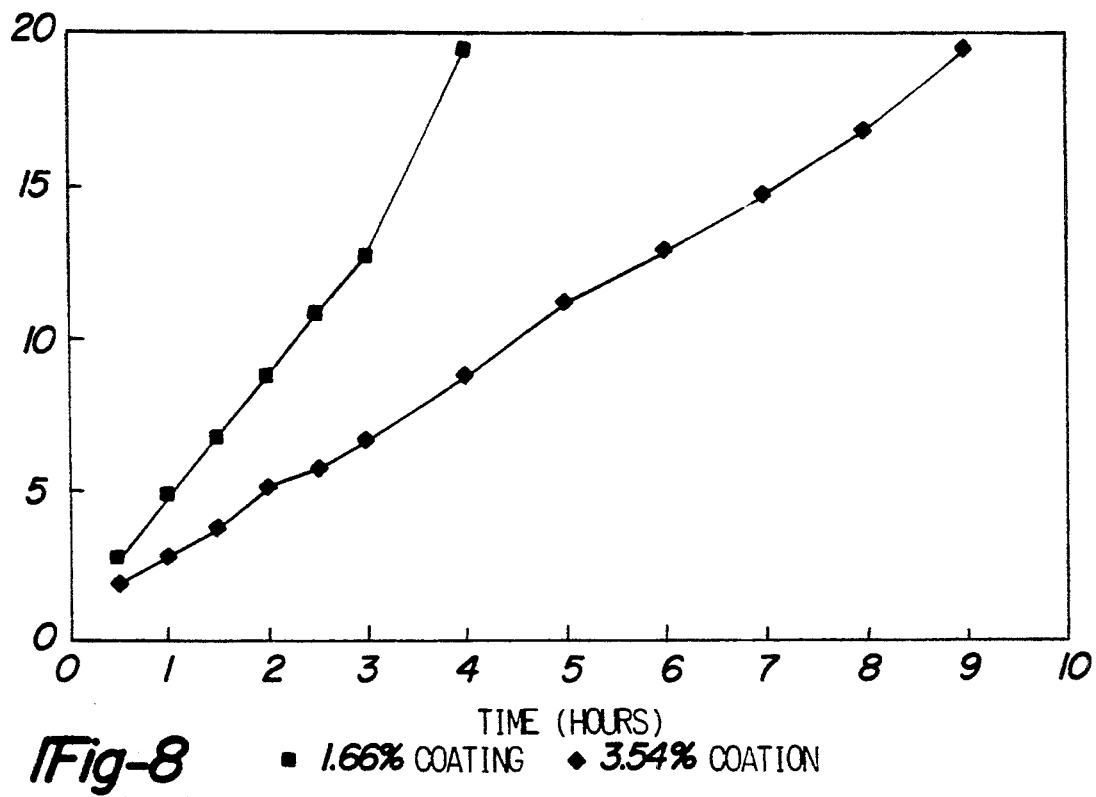

MULTI STAGE DRUG DELIVERY SYSTEM

This is a continuation of copending application Ser. No. 07/826,256 filed on Jan. 27, 1992, now abandoned which is a continuation of Ser. No. 648,968 filed Jan. 31, 1991, now abandoned.

TECHNICAL FIELD

This invention relates generally to drug delivery systems.

BACKGROUND OF THE INVENTION

It has been recognized that there is a need for a drug delivery system which yields an increase in the oral dosing interval of drugs exhibiting presystemic loss metabolism while simultaneously maintaining bioavailability equivalent to the immediate release dosage form. Such drugs would otherwise either require short interval dosing, such as periodic oral dosing having short periods between each oral dosing.

Various drug delivery systems, commonly referred to as time released systems, have attempted to solve this problem by continuously releasing amounts of the drug throughout the travel of the drug through the digestive track. For example, the U.S. Pat. No. 4,773,907 to Urquhart et al, issued Sep. 27, 1988, discloses a delivery system comprising a capsule containing dosage forms comprising a semipermeable wall surrounding a compartment containing drug. A passageway through the semipermeable wall releases drug from the dosage form to the environment. The U.S. Pat. No. 4,777,049 to Magruder et al, issued Oct. 11, 1988, discloses an osmotic delivery system. The system provides a device including a wall which can be a laminate comprising a semipermeable lamina and lamina arrangement with a microporous lamina. The lamina provides micropaths for emitting external fluid into the osmotic device. The device includes an opening having an erodible element, such as a gelatin plug that erodes and forms an osmotic passageway in the environment of use. Within the device is a modulating agent in nonequilibrium proportions. Upon the influx of fluid into the device, there is co-solublization of a useful agent which is then released from the device. Thusly, co-solublization of a modulating agent and a useful agent controls the release of the useful agent and results in the delayed release of the useful agent resulting from a reduction of the concentration of the modulating agent. This results in an osmotic system and a method of preprogramming to a desired time of release, a delayed release or a delayed pulsed release of agent. However, the delayed pulse of release is over a base line release and not a true pulse release from a zero base line.

The U.S. Pat. No. 4,783,337 to Wong et al, issued Nov. 8, 1988, discloses an osmotic system comprising a wall which is at least in part a semipermeable material that surrounds a compartment. An osmotic composition, or several osmotic compositions are contained within the compartment defined by the wall and a passageway in the wall connects the first composition with the exterior of the system. The first composition causes imbibition of fluid which results in the delivery of the suspension or solution through the aforementioned passageway. This can end up being a multi-chamber device.

The aforementioned patents do not result in a truly pulsatile release. Pulsatile release, as used herein, implies an initial first release followed by a period of time where there is absolutely no release. Then, after the predetermined period, there is a true pulse release. Unlike prior art systems, it is desirable to provide a drug delivery system for non-linear presystemic loss drugs which will release fractions of the total dose at specified sites and time in the gastro-intestinal track so that bioavailability will not be compromised by the decreased release rate of conventionally controlled or sustained release dosage forms.

There are several advantages to a true pulsatile delivery system in extending the dosing interval. For those drugs which are first pass metabolized, an increase in delivery rate to the portal system results in a decrease in metabolism. For those drugs exhibiting non-linear prehepatic metabolism a larger fraction of drug will escape metabolism and therefore be available. For those drugs with incomplete absorption due to low permeability, poor solubility or in which case the absorption rate limited by rate of dissolution, enhancers can be added to increase the bioavailability. The pulse time and release rate can be programmed to match the immediate release dosage form profile. The pulse time and release rate from pulsatile delivery can be more reproducible than the immediate release dosage form which relies on patient compliance and rate of gastric emptying for input of drug to the site of absorption, that being the small intestine. The result is a decreased variability in plasma level time curves. The clinical efficacy of a pulsatile delivery system can be established to provide equivalent bioavailability to the conventional dosage form. Accordingly, patient compliance is increased through the use of a reduced and/or simpler dosing schedule. The pharmacodynamics of the pulsatile system can be made to match the established immediate release dosage. Thereby, the metabolic rates equivalent to that obtained from an approved dosing schedule can be obtained, hence no unusual accumulation of metabolites or altered metabolic profile results. The pulse delay and amount being pulsed are programmable to a variety of dosing schedules such that allowance for circadian rhythms is possible in order to optimize the pharmacodynamic response throughout the day. Finally, the optimal dosing schedule for two or more drugs, tailored to their individual pharmacokinetic and pharmacodynamic properties, can be optimized using this technology. The present invention provides an improved means of providing a pulsed dose or doses which are capable of providing all of the aforementioned advantages.

SUMMARY OF THE INVENTION

In accordance with the present invention, there is provided a drug delivery system comprising a first container including an inner chamber for containing a drug therein and having a passageway opening to an external environment thereof. Plug means is disposed in the passageway for plugging and closing the opening. The plug means is releasable from the opening upon the application of pressure from within the inner chamber. The container includes pump means reactive to the external environment for increasing the pressure within the inner chamber and forcing the plug means out of the passageway to release the drug from the chamber and out of the passageway.

The present invention further provides a method of delivering a drug to a body, the method including the steps of ingesting a drug delivery system, immediately releasing a first predetermined amount of drug from a second chamber of the system, and increasing the pressure within a first chamber of the system over time and forcing a plug therefrom at a predetermined time after the ingesting step. The drug is released from the first chamber once the plug is released therefrom.

The present invention further provides a method of making a drug delivery system, the method including the steps of filling a first capsule half with drug and a reactive agent, the capsule being water permeable. The capsule is plugged and a water permeable film is disposed over the capsule and plug. A second capsule half is filled with drug and an open end thereof is releasably mounted over the plugged end of the first capsule half.

FIGURES IN THE DRAWINGS

Other advantages of the present invention will be readily appreciated as the same becomes better understood by reference to the following detailed description when considered in connection with the accompanying drawings wherein:

FIG. 1A is cross sectional view of a drug delivery system made in accordance with the present invention;

FIG. 1B is a cross sectional view of a multichamber drug delivery system made in accordance with the present invention;

FIG. 2 shows the steps of manufacturing the drug delivery system of the present invention;

Figure 4:
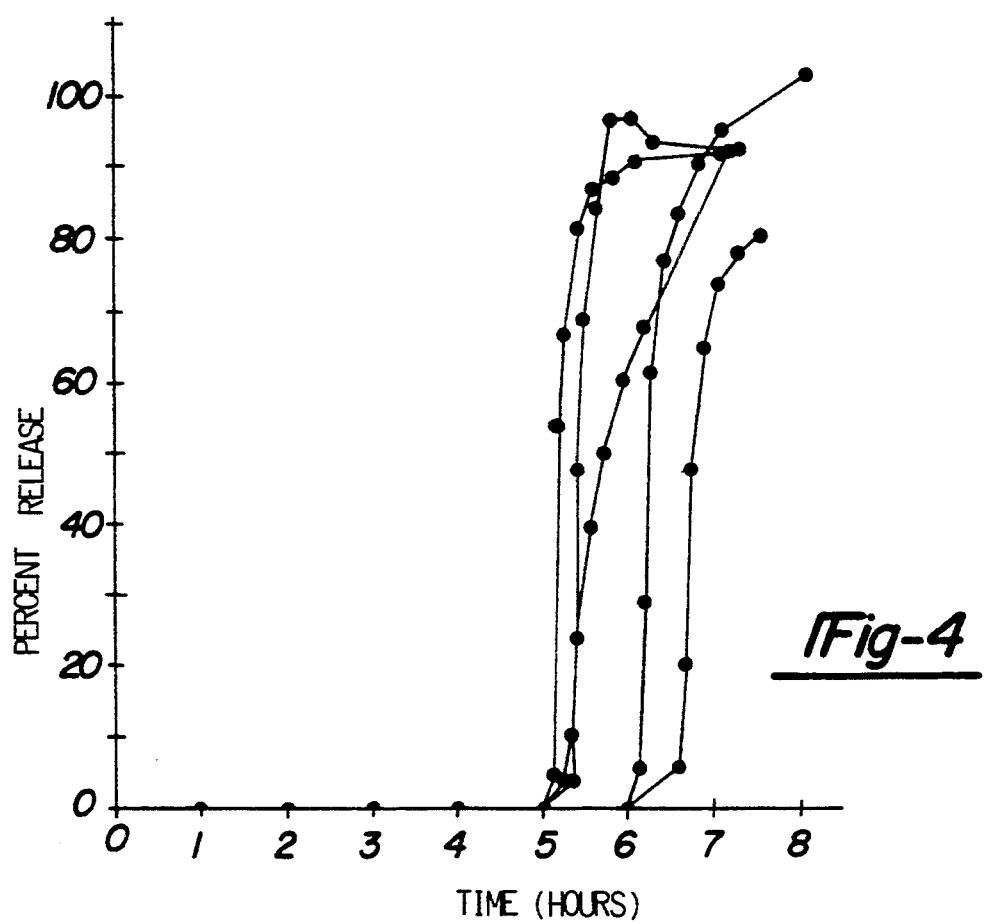
Figure 5:
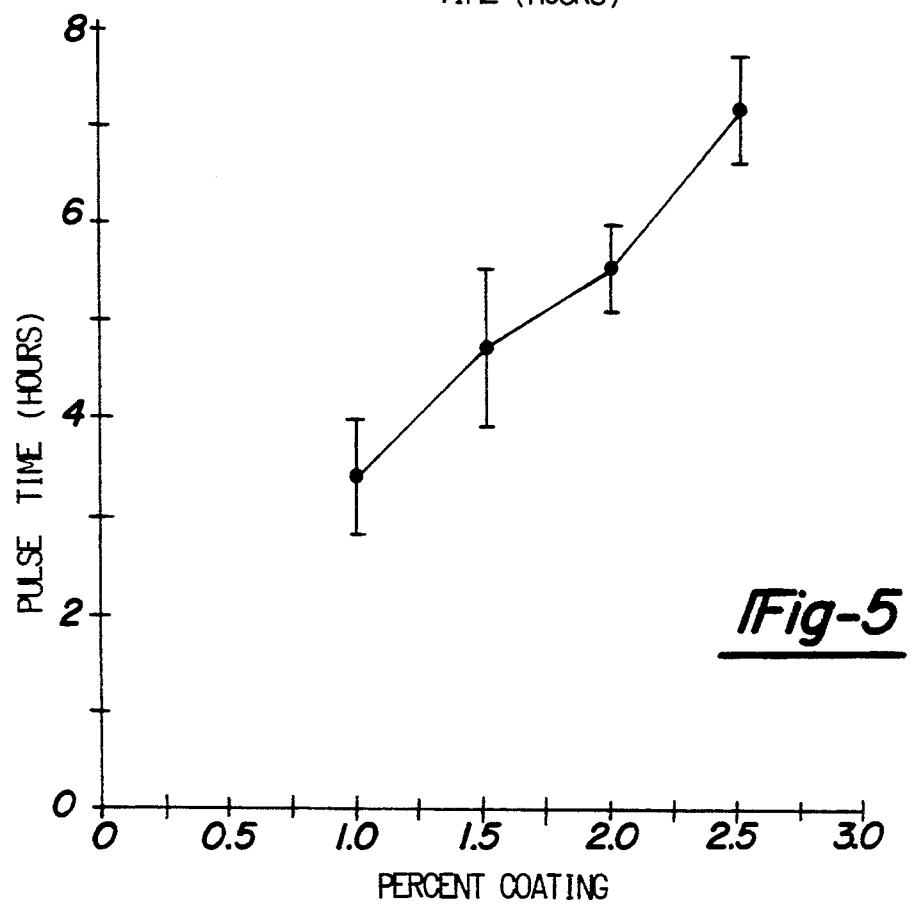
Figure 6:
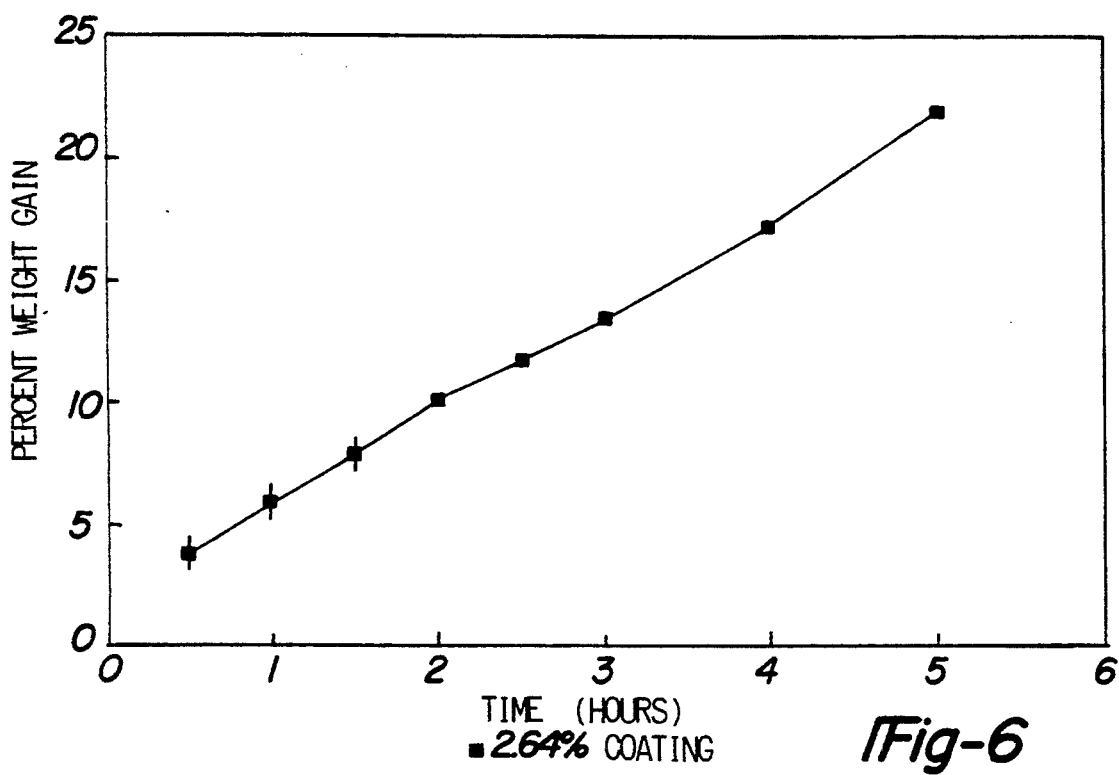
Figure 7:
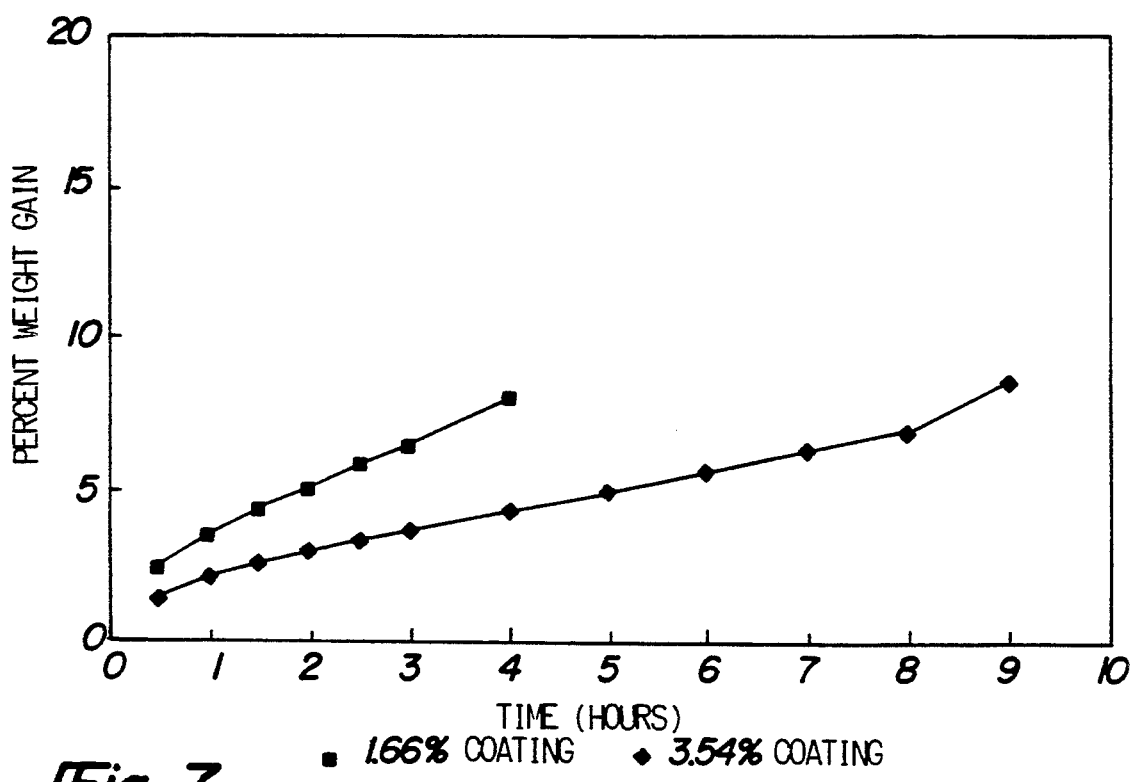
Figure 10:
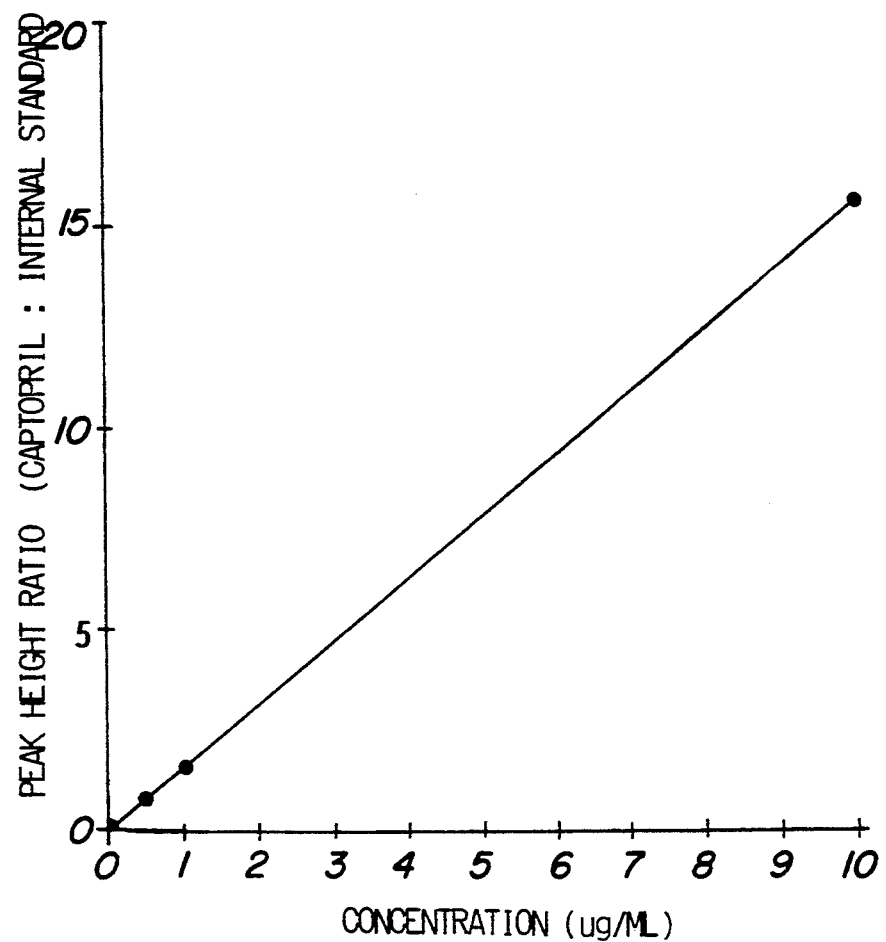
Figure 11A:
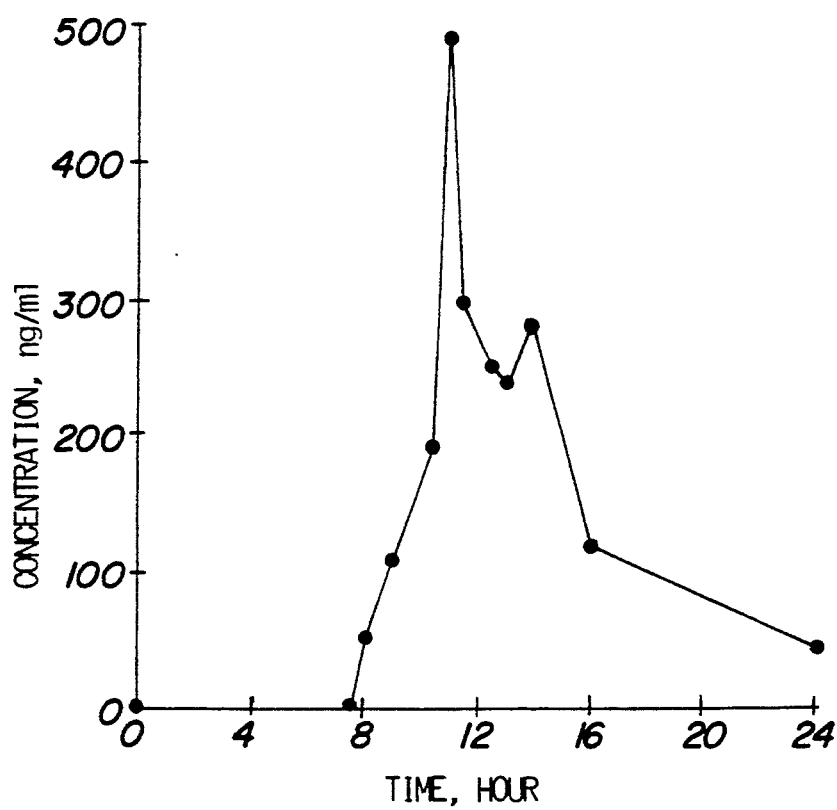

FIG. 3 schematically shows the steps of drug release from the drug delivery system of the present invention over time;

FIG. 4 is a graph showing the percent release of drug from drug delivery systems made in accordance with the present invention over time;

FIG. 5 is a graph showing the average pulse time as function of percent coating;

FIG. 6 shows graphically the results of of water uptake studies on capsules made in accordance with the present invention showing percent weight gain over time;

FIG. 7 shows the results of water uptake studies graphically on lactose filled capsules having different coating weights;

FIG. 8 shows the results of water uptake studies of capsules containing lactose/sorbital therein, the capsules having two different weight coating thereon;

FIGS. 9A and B are chromatograms from blank samples and actual samples from dog studies discussed below;

FIG. 10 shows a plot of chromatographic peak height ratio versus concentration; and FIGS. 11A and B show two graphs illustrating the pulsatile release of drug in vivo.

DETAILED DESCRIPTION OF THE INVENTION

A drug delivery system constructed in accordance with the present invention is generally shown at 10 in the FIGS. This system generally includes a first container in the form of a capsule half 12 and a second container in the form of a mating capsule half 14. The first capsule half 12 includes an inner chamber 16 for containing a drug 18 therein. Of course, the shape of and size of the capsule half can be varied in accordance with the art.

More specifically referring to FIG. 1A, the first capsule half 12 includes a closed end portion 20 extending to a substantially annular wall 22 defining a second open end 24. The wall 22 and opening 24 define an internal passageway 26 opening to the external environment thereof. A plug 28 is disposed in the passageway 26 for plugging the opening 24 closed. The plug 28 is releasable from the opening 24 upon the application of pressure from within the inner chamber 16. The invention is characterized by the first capsule 12 including a mechanism reactive with the external environment for increasing the pressure within the inner chamber 16 and forcing the plug 28 out of the passageway 26 to release the drug 18 from the inner chamber 16 and out of the passageway 26.

As shown in FIG. 1B, the system can include multiple chambers 16,16' and multiple plugs 28,28'. Each chamber 16,16' includes a mechanism reactive with the external environment for first forcing out plug 28 to release the contents of chamber 16 and then sequentially force out the second plug 28' to release the contents of chamber 16'.

With more specific regard to the reactive mechanism, the reactive mechanism can be a pumping mechanism, such as an osmotic means for pumping fluid through the wall of the first capsule half 12 increasing the internal pressure within the inner chamber 16. Accordingly, once the drug delivery system 10 is ingested at a predetermined time, the reactive mechanism will cause a release of the drug 18 from the first capsule half 16 at predetermined time after ingestion. The rate of internal pressure increase results in the release, timing of the rate being controlled by means described below.

For example, to create the osmotic pump of the present invention, the first capsule half 12 includes a membrane film 30 disposed thereover and over the plug 28 for allowing fluid to pass into the inner chamber 16 as a result of an osmotic pressure gradient therethrough. The osmotic pump further includes an osmotic agent 32 disposed within the inner chamber 16 for creating an osmotic pressure gradient across the membrane film 30 and capsule wall when disposed in the fluid of the external environment.

The open end 34 of the second substantially cupped shaped capsule 14 is seated over and in mating engagement with the open end 24 of the first capsule half 12. The second capsule half 14 includes an inner chamber 36 containing drug 18 therein. The second capsule half 14 is releasably connected to the first capsule half 12 so as to release upon ingestion of the capsule thereby providing an immediate release of drug 18 followed after a predetermined time by the pulse release of the drug 18 from the second capsule half 12.

The capsule halves 12,14 can be made from various materials, preferably water containing gelatins.

The plug 28 can be made from various materials which can, in a plug shape, form a friction fit within the passageway 26 of the first capsule half 12. Examples of plug materials are bees' wax and synthetic bees' wax, carnauba wax, partial glycerides and polyethylene glycol (PEG), fatty esters, glyceryl stearate, palmitosterate, paraffin wax, and white wax.

Various osmotic agents can be used with the present invention. Agents such as lactose, sorbitol and mannitol can be used. Optionally, the drug contained within the capsule halves 12,14 may also provide sufficient osmotic pressure thereby obviating the need of an additional osmotic agent.

Further the reactive mechanism can be achieved by other agents. For example, swellable gels can be used. Examples of these agents are acrylic acid polymers, hydroxypropyl methyl cellulose, and ethyl cellulose. Alternatively, gas producing agents can be used, such as sodium bicarbonate. It is possible that these agents or additional agents can be added which effect the environment during release. For example, acidifying agents can be added which would acidify a well defined intestinal area where the pulsed dose is released thereby potentiating absorption of the drug without effecting the remainder of the system. Time release systems cannot achieve this localized effect as the agent would be released throughout the tract and substantially diluted.

Various film materials can be used for forming the membrane film 30. Examples of composition for forming the film materials are cellulose acetate (all grades), cellulose acetate butyrate (all grades), and combinations of the above. Also, ethylcellulose can be used.

Table 1 provides a Listing of 66 drugs which could be used in accordance with the present invention, the list not being an all-inclusive list of such list but rather examples of such drugs.

FIG. 2 schematically illustrates the method of making the drug delivery system 10 in accordance with the present invention. Step A in FIG. 2 shows the first capsule half 12 being empty. Step B shows the capsule half being filled with osmotic reagent 32 and drug 18. As stated above, the drug 18 per se could be the osmotic agent. As shown in Step C, the open end 24 of the first capsule half 12 is plugged with the plug member 28. Step D shows the water permeable film 30 being disposed over the capsule 12 and plug 28. Step D' shows the filling of the second capsule half 14 with the drug 18. Finally, Step E shows the mounting of the open end 34 of the second capsule half 14 over the plugged end 24 of the first capsule half 12.

Of course, many of the steps shown in FIG. 2 can be accomplished by various filling, plugging, and coating methods. For example, Table 2 shows the composition of a preferred captopril containing capsule made in accordance with the present invention. The capsule was made by the following specific method. Also, multi-chambered systems can be made by repeating the filling and coating steps.

Weighed citric acid, anhydrous, USP, was disposed in a mortar and ground thoroughly to a fine powder. Anhydrous lactose, USP, microcrystalline cellulose, NF, sorbitol, NF, Croscarmellos sodium, NF, were added to the mortar containing the citric acid, anhydrous, USP and mixed well. The captopril, USP was added to the mortar containing the excipients of the previous step and mixed thoroughly. The magnesium stearate, BP was added to the mortar and stirred gently. Homogeneity of the mixture was checked from three spots in the mortar taking one gram sample. A 98.4% yield was obtained.

A number zero hard gelatin two piece capsule was filled with 350 mg±1.5 mg of the fill mix or adjusted to give a potency of 67 mg based on the assay result from the previous step. Utilizing the ingredients set forth in Table 2, a plurality of capsules were filled.

Gelucire 50/02 was melted using a water bath to a constant temperature of 60° C.±5° C. 120 mg of the melted gelucire 50/20±20 mg was filled into each capsule or five drops or the Gelucire was dispensed using a transfer pipette into each capsule. The capsules were allowed to sit until the gelucire sufficiently solidified. The specific weight (amount) of Gelucire or other plug material can be varied. The capsules were weighed and then placed in a 6 inch diameter coating pan. Rotation of the coating pan was started and adjusted to a speed of 30 rpm±5 rpm. Using a Sigma Glass Spray Unit, the bottle was filled with 225 ml±25 ml coating solution. A spray top was fitted on the bottle and tightly capped. A suitable spray pattern was obtained using a compressed air unit by adjusting the air flow and the capsules were sprayed in the pan for 60 seconds. The capsules were allowed to turn in the pan with a stream of compressed air blowing into the pan for 60 seconds. The weight gain of the capsules was calculated as follows:

$$\% \text{ gain} = \frac{\text{coated weight} - \text{uncoated weight}}{\text{uncoated weight} \times 100}.$$

Thusly, when referring to coating thickness, percent coat is referenced, that meaning the percent gain in weight of the capsule coated by the membrane film. The greater the percent gain, the thickener the coating on the capsule.

To make the final capsules, 66 mg±1 mg of the captopril immediate release blend (50%) was disposed into the cap of the size number zero hard gel and mounted onto the capsule previously referred to. The cap was placed on the body taking care not to lose any of the material in the cap or to disrupt the coating on the capsule body. These fine finished capsules were stored in polyethylene bags until tested as described below.

FIG. 4 shows the effective ability of the capsules made in accordance with the present invention to generate a pulse release. First capsule halves 12 made in accordance with the method previously described were tested in vitro for ability to create an osmotic pressure therein to force the release of the plug member 23 and thereby release captopril therefrom. The method consisted of the steps of disposing capsule halves coated as previously described in 28 ml of pH 6.5 buffer solution at 37° C. Samples were initially taken once every hour. At the 5 hour time period, samples were taken every 10 minutes.

As shown in FIG. 4, there is absolutely no release from the capsules during the first 5 hours of testing. There was an immediate pulsatile release from the capsules beginning at 5 and 6 hours. Accordingly, capsules made in accordance with the present invention have the capacity to pulse release.

Several variables were evaluated with regard to the manufacturing techniques to determine their effect on pulse time. The results of these tests are shown in Table III.

As shown in Table III, plug variables such as the effect of the hydrophilic/lypophilic balance HLB of the plug on pulse time was tested. The HLB values were varied by varying the components used to make the plug. For example, different waxes have different HLB values. By combining different waxes, the HLB value of the resulting plug is varied. Specific examples are set forth in Table V. Additionally, the temperature of the plug material, such as gelucire, prior to filling also effects pulse time.

Table III also shows the effect of coating variables such as spray rate, solids content and plasticizer content of the coating. What is also evident from Table III is that the variables tested were also effected by the percent coating, that is, the weight percent of the coating as compared to the weight of the remainder of the capsule.

A more detailed analysis of the average pulse time as a function of percent coating is shown in FIG. 5. FIG.

5 shows an almost linear relationship between increased percent coating and pulse time. Thusly, one method of controlling the predetermined time of release is by changing the percent coating of the capsule. As in the prior experiments, this experiment was conducted by coating capsules as described above, determining their percent coating and the placing the capsules as batches based on their percent coating in 20 ml of buffer, 6.5 pH at 37° C. Captopril release was monitored by high pressure liquid chromatography.

Further studies were conducted on the effect of various osmotic agents as they effect water uptake within capsules. To perform these experiments, capsules as made above but filled with lactose, and lactose/sorbitol filled capsules were disposed in 20 ml of buffer, pH 6.5, at 37° C. Six of each capsule type were placed in buffer, the lactose filled capsules and the lactose/sorbitol filled capsules having either a 1.66 weight percent coating or 3.54 weight percent coating. After the periods of time indicated in FIGS. 6–8, the weight of the capsule was determined and percent weight gain was determined as showing comparative rates of the osmotic pressure gradients created by the various agents within the capsules.

FIG. 6 shows an almost linear weight percent gain over time of the Captopril capsules, containing both lactose and sorbitol therein as discussed above. FIG. 7 shows a comparative decrease in weight percent gain over time in the capsules containing only lactose. The expected increase in rate is shown with capsules having the thinner coating of 1.66%. A similar phenomenon is shown with the lactose/sorbitol filled capsules, except that these capsules had a significant increase in rate compared to capsules containing lactose alone.

In view of the above data, the rate of the internal pressure gradient increase and the time period to release the plug member can be adjusted and controlled by adjusting the amount and type of osmotic agent within the capsules, as well as adjusting the thickness of the membrane coating.

The present invention further provides a method of delivering a drug to a body, as schematically shown in FIG. 3. The steps generally include the ingestion of the drug delivery system 10 as shown in FIG. 3. FIG. 3 shows the delivery of the drug over a time, the time line being schematically shown at the bottom of the FIG. There is an initial release of the first predetermined amount of drug 18 from the first chamber 36 of the system 10 after ingestion. The first capsule half 12 remains intact within the membrane 30. As the first capsule half 12 travels through the digestive track it is exposed to the fluid therein, there is a pressure buildup within the inner chamber 16 of the system 10 over time. This forces the plug 28 from the passageway 26 at a predetermined time after the ingesting step. Finally, after the predetermined time, the plug 28 is completely forced from the passageway 26 thereby releasing the drug 18 from the inner chamber 16. A multichamber system works in the same manner with a later pulse of drug 18' being released from chamber 16' and plug 28' is forced out of the capsule half 12. As shown by the in vitro experiments above, the rate of osmotic pressure increase of the inner chamber 16 can be controlled by various variables such as the type and amount of osmotic agent as well as the thickness or percent coating of the membrane film 30.

Applicant has conducted bioavailbility studies demonstrating the aforementioned method in vivo.

MATERIALS

Capsules, prepared as described above numbered from 3 to 7, were used for bioavailability study. Captopril tablets and powder for oral and intravenous studies were kindly donated by Squibb. Two male beagle dogs, weighing 34 and 30 pounds and two midgut-fistulated female dogs, weighing 47 and 38 pounds respectively, were employed for the bioavailability studies. These dogs were fasted over 15 hours before experiments were began.

Oral study—Four tablets containing 25 mg of Captopril were given to four dogs orally with 20 ml of tap water. Dogs were released from restraining sling for 15 minutes four hours after the experiment was started for urination and a walk. Blood samples (1.2 ml) were collected through the forearm vein, which was catheterized with an 18G catheter (Abbott, Chicago, Ill.), at 0, 0.25, 0.5, 1, 1.5, 2, 2.5, 3, 3.5, 4, 5, and 6 hours and transferred to test tubes containing 5 mg of each N-ethylmaleimide (NEM) and ethylene diamine tetra acetic acid (EDTA) sodium and stored in a freezer until assay.

Intravenous study—50 mg of captopril powder was dissolved in 15 ml of saline and filtered through 0.22 um sterilized filter paper right before the infusion was started. For each four dogs, this solution was infused over 15 minutes into the catheterized forearm vein using a Harvard infusion pump. For this intravenous study, blood samples were collected from the other side of the forearm vein at 0, 1, 2, 3, 5, 8, 10, 13, 15, 16, 18, 20, 23, 25, 30, and 40 minutes and at 1, 2, 3 and 4 hours.

The study was duplicated in each dog. The experimental design was the same as the oral study except that the schedule for sample collection was every one hour for 12 to 13 hours. Dogs were released from the sling every four hours for 15 minutes.

GC-EC blood sample assay—All blood samples were assayed using gas chromatography with an electron-captured detector. The GC-EC assay, which was reported earlier by Bathala et al., was slightly modified and tested for linearity, precision, and accuracy. The standard curve was linear over the concentration range studied, with an r value of 0.9999. The detection limit based on a signal-to-noise ratio of 3 were 25 ng/ml. The determination of Captopril was highly reproducible, with a CV of less than 7% for all concentrations examined. The intra-and inter-day variability of the Captopril assay was not significant.

Materials—NEM, hexafluoro-2-propanol, trifluoro acetic anhydride, were reagent grade (Sigma Co., Mo.) and used as received. All other chemicals were reagent grade (Fisher Scientific, Chicago) or HPLC grade. Captopril and internal standard, SQ 25761, were obtained from E. R. Squibb & Sons (Princeton). The chromatographic column was capillary, 30 m×0.53 mm i.d. (1.2 mcl of film thickness), immobilized with 100% dimethyl polysiloxane (Cat. #19656, Alltech Assoc., Chicago Ill.). Nitrogen and argon-methane (95:5) of the highest available purity (Metro Welding Co., Detroit, Mich.), were used.

Equipment—Gas chromatography was preformed using HP 5890A (Hewlett Packard) gas chromatograph equipped with a nickel-63 electron-capture detector, 3393A HP integrator, 7673A HP controller, and 7673A HP automatic sampler. All extractions were carried out by shaking the samples on a Tekmar mixer (Janke & Kunkel Co., Funkenstort, West Germany). The N-Evap (Organomation Assoc., Northborough, Mass.)

was used to remove benzene from extracts with a nitrogen stream. The esterification with hexafluoro-2-propanol were performed by incubating in a heating block (Lab-Line Instruments Inc., Melrose Park, Ill.).

Blood sample assay—After thawing blood samples by sonication, the blood was diluted with distilled water (1:1 by volume). An internal standard (615 ng/ml) was spiked into blood samples and excess NEM and naturally occurring interfering substances were removed by extraction with benzene followed by acidification and extracted with benzene and converted to their hexafluoroisopropyl esters. These were separated by GC-EC. Standard curves from spiked Captopril concentrations of 0.05. 0.5, 1, 10 mcg/ml in blood were prepared for daily working standards. For reproducibility studies, four concentrations for the standard curve were assayed in quadruplicate using the method described.

Data analysis—Area under curves (AUC) of time zero to t and time zero to infinitive by extrapolating the last blood concentration with an elimination rate constant (ke) were evaluated from the oral, intravenous, and technology studies based on the noncompartmental analysis. Relative bioavailability of technology capsules were determined comparing to the oral study and normalized by the dose given.

In view of the experimental results, it can be concluded that capsules made in accordance with the present invention provide a pulsatile release of drugs effective in vitro environments, as well as in vivo. Such a drug delivery system possess great potential for use in providing drugs to the public that have a first pass effect.

GC-EC assay described above with a slight modification using capillary column, was adequate for the present study. Typical chromatograms from blank blood samples and actual samples from dog studies are shown in FIG. 9A and B respectively. The retention times of the derivatized captopril and internal standard were about 6.2 and 9.6 minutes, respectively. These retention times are different from those reported earlier by Bathala et al. This is probably due to the alteration in instrumentations. No interfering peaks were observed in the extracts of the blank dog blood. The derivatives of captopril and of internal standard were stable over one month (testing period) at room temperature.

A plot of chromatographic peak height ratio versus concentration was linear for captopril from 0.05 to 1 mcg/ml (FIG. 10). The correlation coefficient and the y-intercept for the straight lines were 0.999 and 0.003, respectively. The average coefficient of variation (CV) for all the concentrations examined was +7%. The linearity and reproducibility of the GC-EC method in dog blood by Bathala et al., was demonstrated by 4 consecutive calibration curves in FIG. 2.

Figure 11B:
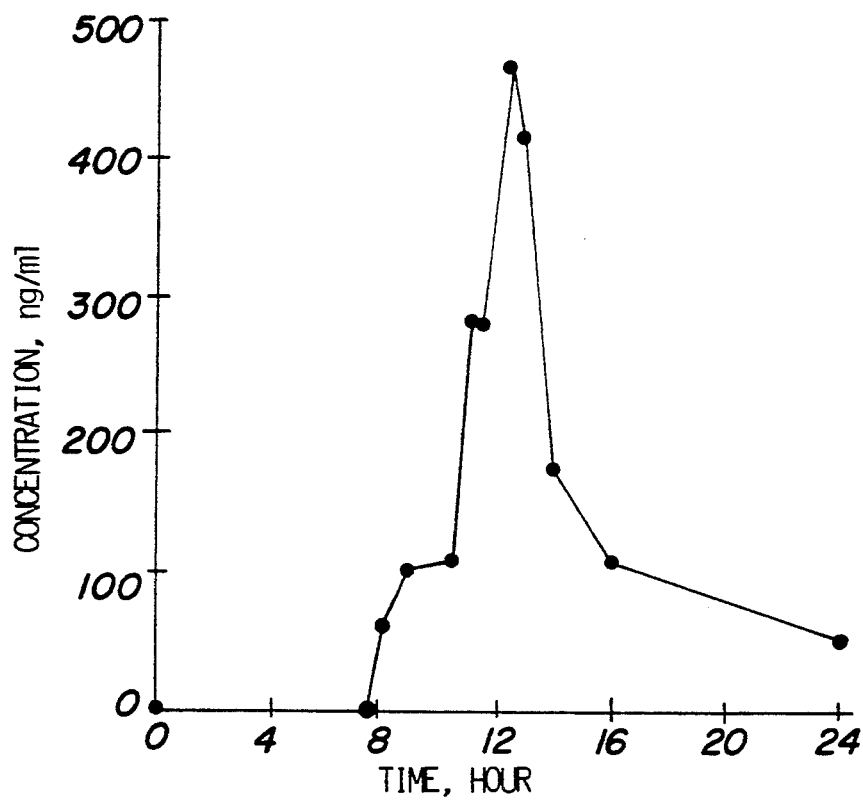

FIGS. 11A and 11B show the results of two dog studies wherein capsules made in accordance with the present invention were ingested. The capsules contained captopril and were made as discussed above. Blood samples were analyzed at the times indicated. There was no release of drug prior to the eight hour time point followed by a pulse or peak of drug. The pulse was a well defined peak. Accordingly, the present invention has been shown to function in vitro as well as in vivo.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

TABLE I

| 66 DRUGS WHICH HAVE A FIRST-PASS EFFECT | |
|---|---|
| ALDOSTERONE | MEPERIDINE HCL |
| ALPRENOLOL | 6-MERCAPTOPURINE |
| AMITRYPTYLINE | METAPROTERENOL SULFATE |
| ASPIRIN | METHOXAMINE HCL |
| BECLOMETHASONE DIPROPIONATE | METHYLPREONISOLONE (F≈0.85) |
| BROMOCRIPTINE MESYLATE (F≈0.06) | METHYLTESTOSTERONE |
| BUTORPHANOL TARTRATE | METOPROLOL TARTRATE |
| CHLORPROMAZINE HCL | MORPHINE SULFATE |
| CIMETIDINE (F≈0.7) | NALBUPHINE HCL |
| CODEINE | NALOXONE HCL |
| CORTISONE | NEOSTIGMINE |
| CYCLOBENZAMINE HCL | NIFEDIPINE |
| DESMETHYLIMIPRAMINE | NITROGLYCERIN |
| DIHYDROERGOTAMINE MESYLATE | NOREPINEPHRINE BITARTRATE |
| DILTIAZEM HCL | NORETHINDRONE (F≈0.65) |
| DOBUTAMINE HCL | NORTRIPTYLENE HCL |
| DOPAMINE HCL | OXPRENOLOL |
| EPINEPHRINE | OXYPHENBUTAZONE |
| ERGOLOID MESYLATES | PENICILLAMINE |
| ERGOTAMINE TARTRATE | PENTAZOCINE HCL & LACTATE |
| ESTRADIOL | PHENACETIN |
| ETHINYLESTRADIOL (F≈0.4) | PHENTOLAMINE HCL & MESYLATE |
| FLUNISOLIDE | PHENYLEPHRINE HCL & BITARTRATE |
| FLUOROURACIL | PREDNISONE (F≈0.85) |
| 5-FLUORO-21-DEOXYURIDINE | PROGESTERONE |
| GUANETHIDINE SULFATE | PROPOXYPHENE HCL & NAPSYLATE |
| HYDRALAZINE HCL | PROPRANOLOL HCL |
| IMIPRAMINE HCL | RITODRINE HCL |
| ISOETHORINE HCL & MESYLATE | SALICYLAMIDE |
| ISOPROTERENOL SULFATE | SALBUTAMOL |
| ISOSORBIDE DINITRATE | TESTOSTERONE |
| LEVALLORPHAN TARTRATE | TIMOLOL MALEATE |
| LIDOCAINE HCL | VERAPAMIL HCL |

SOURCE OF INFORMATION WAS DRUG INFORMATION 84, AMERICAN HOSPITAL FORMULARY SERVICE, AMERICAN SOCIETY OF HOSPITAL PHARMACISTS.

TABLE II

| | |
|---|---|
| Captopril, USP* | 67.00 |
| Citric Acid, Anhydrous, USP | 100.00 |
| Lactose, Anhydrous, USP | 41.00 |
| Microcrystalline Cellulose, NF | 97.35 |
| Sorbitol, NF | 35.00 |
| Croscarmellose Sodium, NF | 7.00 |
| Magnesium Stearate, BP | 1.75 |
| Gelocire 50/02 | 120.00 |
| Size #0 hard gelatin two piece capsules | 66.00 |
| Captopril immediate release blend (50%) | |
| Coating solution for captopril pulsatile release capsules | q.s. to obtain suitable release |

*Microcrystalline cellulose weight to be adjusted based on captopril, USP potency.

TABLE III

Pulsatile Delivery System - variable evaluation:

| Variable | % Coat | Pulse Time | n |
|---|---|---|---|
| Plug Variables: | | | |
| Hydrophilic/Lipophilic Balance (HLB of The Gelucire) | | | |
| 5.5 | 2.80% | 5.00 | 16 |
| 4.0 | 2.75% | 3.95 | 33 |
| 2.0 (current formula) | 2.82% | 6.07 | 12 |
| Temperature of the Geluicre prior to filling | | | |
| 85° C. | 2.78% | 6.52 | 17 |
| 75° C. | 2.82% | 6.07 | 12 |
| 60° C. (current procedure) | 2.85% | 3.42 | 24 |
| Coating Variables: | | | |
| Spray Rate | | | |
| Slow (0.038%/appln. | 3.02% | 3.15 | 48 |
| Fast (0.12%/appln. | 2.93% | 4.43 | 43 |
| (Current appln. rate is 0.080%) | | | |
| Solids Content (C. acetate, C. acetate butyrate) | | | |
| 2.8% | 1.0% | 1.07 | 6 |
| | 1.8% | 2.65 | 6 |
| | 2.6% | 3.66 | 6 |
| (Current formula has a 4.2% solids content) | | | |
| Plasticizer | | | |
| 4% PEG 200 | 1.11% | 1.71 | 6 |
| | 1.91% | 3.47 | 6 |
| 0% PEG 200 | 1.13% | 3.01 | 5 |
| (current formula) | 1.46% | 5.04 | 7 |

TABLE IV

Examples of mixtures of plug materials to control HLB value

| | Plug Material | HLB |
|---|---|---|
| 1. | Partial glycerides and PEG fatty esters | 10 |
| 2. | Partial glycerides and PEG fatty esters | 6 |
| 3. | Glyceryl stearate | 2 |
| 4. | Glyceryl palmitostearate Mixtures of the above materials can be mixed together to achieve Plug materials of varying HLB values. | 2 |
| 5. | 50% Partial glycerides and PEG fatty esters (HLB 10) and 50% Glyceryl sterate | 6 |
| 6. | 50% Partial glycerides and PEG fatty esters (HLB 6) and 50% Glyceryl palmitostearate | 4 |

What is claimed is:

1. A drug delivery system (10) consisting essentially of; a first container (12) defining at least one inner chamber (16) for containing drug (18) therein and having a passageway (26) opening to an external environment thereof, said container (12) being fluid permeable; a second container (14) having an open end (34) releasably mounted on said first container (12) and closed thereby for forming a closed second chamber (36) therewithin for containing drug (18), said second container (14) being releasable from said first container (12) upon ingestion to release drug (18), and a fluid impermeable plug (28) disposed in said passageway (26) for plugging said opening (24) closed, said plug (28) being slidably releasable from said opening (24) upon the application of fluid pressure from within said inner chamber (16), said plug being selected from the group consisting of higher fats, waxes, fatty esters, said container (12) including an osmotic reagent for increasing the pressure within said inner chamber (16) when disposed in a fluid environment and forcing said plug (28) to slide out of said passageway (26) to release the drug (18) from said inner chamber (16) and out of said passageway (26) in a pulse of minutes to about 15 hours from initial contact of said container (12) with the fluid.

2. A system as set forth in claim 1 wherein said osmotic agent (32) is selected from the group consisting of lactose, sorbitol and mannitol.

3. A system as set forth in claim 1 wherein said inner chamber contains a medicament defining said osmotic reagent.

4. A system as set forth in claim 1 further including film disposed over said container, said film being selected from the group consisting of cellulose acetate, cellulose acetate butyrate, and ethylcellulose.

5. A system as set forth in claim 4 wherein the thickness of said film is inversely related to the rate of travel of said plug.

6. A system as set forth in claim 1 further including a swellable agent disposed within said inner chamber (16).

7. A system as set forth in claim 6 wherein said swellable agent is selected from the group consisting of acrylic acid polymers, hydroxypropyl methyl cellulose, and ethyl cellulose.

8. A system as set forth in claim 1 including a reactive agent disposed within said inner chamber capable of causing an increase in internal pressure within said inner chamber.

9. A system as set forth in claim 8 wherein said reactive agent is sodium bicarbonate.

10. A system as set forth in claim 1 wherein said first container (12) includes more than one inner chamber (16,16') for containing drug in each chamber, a plug (28,28') being disposed in said passageway (26) for plugging and separating each of said inner chambers (16,16') and pressure creating means in each of said inner chambers.

11. A method of delivering a drug to a body by: ingesting a drug delivery system (10); releasing a first amount of drug (18) from a first chamber (36) of a system (10); actively drawing fluid through a wall of a second chamber (16) of the system (10) and increasing the internal pressure within a second chamber (16) of the system (10) from minutes to about 15 hours and forcing a plug (28) to slide out therefrom at a time from minutes to about 15 hours after said ingesting step, the plug being selected from the group consisting of higher fats, waxes, fatty esters; and releasing drug (18) from the second chamber (16) once the plug (28) is released therefrom.

12. A method as set forth in claim 11 wherein a cup-shaped capsule (12) defines said first chamber (16) and includes a plug (28) disposed in an open end (24) thereof and a membrane film (30) disposed completely thereon, said controlling step being further defined as increasing the thickness of the film (30) for slowing the rate of increasing pressure with the first chamber (16) and delaying the release of the plug (28) therefrom.

13. A method as set forth in claim 11 wherein said step of increasing pressure is further defined as creating osmotic pressure across the container wall between the second chamber (16) and the external environment, the increasing pressure created thereby forcing the plug (28) from the container (12).

14. A method as set forth in claim 13 wherein said controlling step is further defined as varying an osmotic agent (32) for being disposed within the second chamber (16) for creating an osmotic gradient for increasing or decreasing the rate of increasing osmotic pressure.

15. A method as set forth in claim 11 wherein said controlling step is further defined varying the amount of a swellable agent disposed within the second chamber (16).

16. A method as set forth in claim 11 wherein said controlling step is further defined as varying the amount of a gas producing agent within the second chamber (16).

17. A method as set forth in claim 11 wherein said releasing step is further defined as releasing an agent that effects an environment of said system (10) at the time of release and effecting the efficacy of the released drug.

18. A method as set forth in claim 17 wherein said step of releasing an agent is further defined as releasing an acidifying agent to acidify the area immediately about said released drug and potentiating absorbtion of the drug without effecting the remainder of the body.

* * * * *